United States Patent [19]

Rodriguez et al.

[11] Patent Number: 4,823,624
[45] Date of Patent: Apr. 25, 1989

[54] MATERIAL LAYER VOLUME DETERMINATION WITH CORRECTION BAND

[75] Inventors: Rodolfo R. Rodriguez, Randolph; Matthew W. Lesniesky, Stanhope; Charles F. Galanaugh, West Milford, all of N.J.; Robert A. Levine, Guilford; Stephen C. Wardlaw, Old Saybrook, both of Conn.; Theodore Juraschek, Wyckoff, N.J.

[73] Assignee: Becton Dickinson & Company, Parsippany, N.J.

[21] Appl. No.: 248,632

[22] Filed: Sep. 26, 1988

Related U.S. Application Data

[62] Division of Ser. No. 68,572, Jul. 1, 1987, Pat. No. 4,774,965.

[51] Int. Cl.$^4$ ............................................. A61B 5/14
[52] U.S. Cl. ................................. 73/865.9; 73/1 H
[58] Field of Search ............ 73/149, 1 J, 1 H, 61.1 R, 73/866, 865.8, 865.9; 128/771, 637; 210/927, 789, 782; 356/36, 39, 427, 40; 436/63, 177; 494/10, 37, 43; 33/1 BB, 125 A, 125 R

[56] References Cited

U.S. PATENT DOCUMENTS

| | | | |
|---|---|---|---|
| 3,741,011 | 6/1973 | Seybold | 73/149 |
| 4,027,660 | 6/1977 | Wardlaw et al. | 73/149 |
| 4,077,396 | 3/1978 | Wardlaw et al. | 73/149 |
| 4,082,085 | 4/1978 | Wardlaw et al. | 73/61.1 R |
| 4,567,754 | 2/1986 | Wardlaw et al. | 73/61.1 R |

Primary Examiner—Stewart J. Levy
Assistant Examiner—Robert R. Raevis
Attorney, Agent, or Firm—William W. Jones

[57] ABSTRACT

A centrifuge tube is used to hold a mixture of several constituents, and also contains a generally cylindrical float. The float settles, after centrifugation, into the zone occupied by the constituent whose volume is to be measured. The constituent layer will settle, after centrifugation, into the annular space between the tube bore and the outside of the float, and will be expanded axially due to the restricted volume of the annular space. The degree of expansion is dependent upon the respective sizes of the float O.D. and the tube bore ID, both of which must be closely controlled for accurate results. A known volume of a control material is placed in the tube to settle into the annular space during centrifugation in an area thereof outside of the constituent layer zone. The length of the band of the control material is measured after centrifugation and is compared to a known length which will result if the annular space is of the proper target volume. A correction factor is thus obtained and applied to all of the other constituent layers which were measured. The band thus forms a varying reference which reflects the actual volume of the annulus.

1 Claim, 1 Drawing Sheet

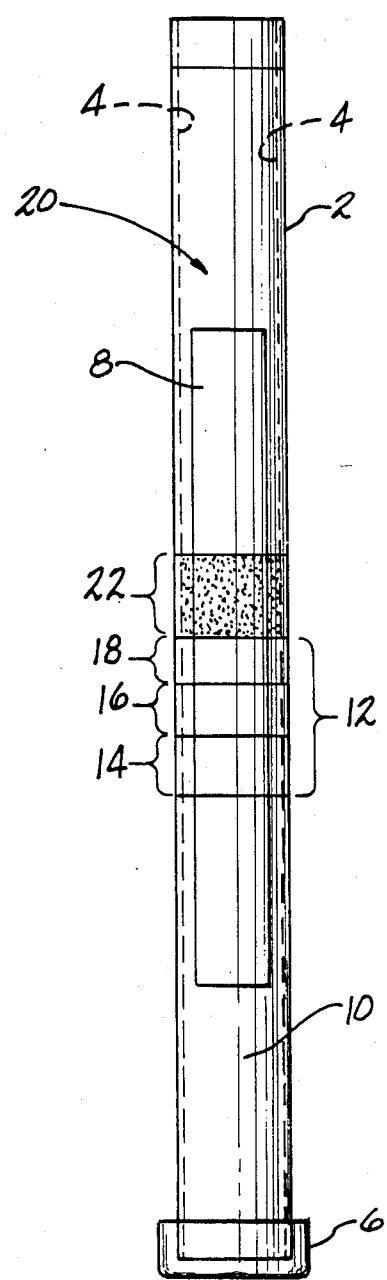

MATERIAL LAYER VOLUME DETERMINATION WITH CORRECTION BAND

This application is a division of application Ser. No. 068,572, filed July 1, 1987, now U.S. Pat. No. 4,774,965 issued on Oct. 4, 1988.

This invention relates to the measurement of one or more constituent layers in a complex material mixture, and more particularly, to volumetric measurements in a centrifuged sample, with the application of correction factors to correct for dimensional variations in the paraphenalia used to contain the sample.

BACKGROUND ART

A technique has been devloped to measure constituent layers in a complex material mixture by centrifuging a sample of the material mixture in a capillary or other tube which contains a float. The float is preferably cylindrical and of a specific gravity which causes it to settle into the centrifuged mixture to a degree which creates a free volume annulus in the tube into which the layer, or layers to be measured will settle. The layers to be measured are thus physically elongated, and can be more easily and accurately measured. This technique is described in U.S. Pats. Nos. 4,027,660, issued June 7, 1977; 4,082,085 issued Apr. 4, 1978; 4,156,570 issued May 29, 1979; and others.

This technique, as described in the prior art, depends on the manufacturer's ability to hold the capillary tube ID's and the float OD's to very tight tolerances. The magnification factor for the elongated constituent layers, when the technique is used as preferred in its commercial form, is about 10.5. This means that any layer which is expanded by the technique will be 10.5 times longer using the float than it would be without using the float. In order to achieve this magnitude of elongation, the tube ID will be maintained at 0.06605 inch, and the float OD will be maintained at 0.06285 inch. Thus the annulus is preferably only sixteen ten thousands of an inch thick. It will be appreciated that minor variations in either the tube ID or the float OD, especially if additive, can result in changes in the annulus thickness which can cause inaccurate readings. For example, a tube ID which is slightly oversize, i.e. 0.00016 inch too large, plus a slightly undersized float, i.e. 0.00011 too small, will result in a reduction of the observed band lengths in the annulus of 8%.

DISCLOSURE OF THE INVENTION

This invention relates to a technique for providing an internal standard correction band in the tube which resides in the annulus after centrifugation, but separate from any constituent layers of the material which are to be measured. In a blood sample, the correction band may, for example, float on top of the lightest of the constituents being measured, i.e. the platelets, and would thus form an additional visible band adjacent to the platelets which band would have its length measured. The correction band is formed by placing a known volume of artificial beads, (or some other flowable material such as a liquid or gel which is immiscible with the blood, or other material being measured) which can be made from plastic, in the tube prior to centrifugation. The beads will have a common controlled size, or a statistically repeatable heterogeniety and may be differentially colored, preferably fluorescent, so as to be readily contrasted with the other colored bands in the tube formed by the stained layered material constituents. The material from which the beads are made will a specific gravity such that the beads will float on one of the constituent material layers away from those being measured, so as not to interfere with the constituent measurements being performed. As previously noted, in the blood sample, the beads will be made to float on the platelet layer. The volume of beads placed in the tube will be constant, such that the beads will form a correction band of known length when the tube ID and the float OD are made to specification. Any variations in the tube and float which enlarge or shrink the annulus will be reflected in the length of the correction band. The measurements can be made and the corrections applied in an instrument such as that disclosed in U.S. Pat. No. 4,156,570; or that disclosed in U.S. Pat. No. 4,558,947, both of which are incorporated herein by reference.

It is therefore an object of this invention to provide an improved technique for measuring centrifuged material constituent layers which employs means for identifying incorrect readings resulting from dimensional variations in the paraphenalia used to contain the samples.

It is a further object to provide an improved technique of the character described wherein a correction band is formed in the tube which contains the sample being measured.

It is an additional object of this invention to provide an improved technique of the character described wherein the correction band is formed with a preset volume of artificial beads which settle into the measurement area of the tube but outside of the constituent layers which are being measured.

It is another object of this invention to provide an improved technique of the character described wherein the correction band expands or contracts in response to dimensional variations in the measuring zone whereupon appropriate corrections can be made to the measured lengths of the constituent layers.

BRIEF DESCRIPTION OF THE DRAWING

These and other objects and advantages will become more readily apparent from the following detailed description of a preferred embodiment of the invention when taken in conjunction with the accompanying drawing which is an enlarged elevational view of a tube and float combination incorporating a correction band in accordance with the invention.

BEST MODE OF CARRYING OUT THE INVENTION

In the drawing, the tube 2 is a glass capillary tube which is formed with a nominal target ID or bore diameter of 0.066050 inch, the tube bore being designated by the broken lines 4. The bottom of the tube 2 is closed with a cap 6 after the blood sample has been drawn into the tube 2. The float 8 is formed from a plastic material having a specific gravity which causes it to float in the red cell layer when the blood sample is centrifuged and is formed with a nominal target OD of 0.06285 inch. After centrifugation, the white cell layer, or buffy coat, will layer out into three separate bands on top of the red cell layer 10. The buffy coat 12 will layer out into a granulocyte layer 14, a leukocyte/monocyte layer 16, and a platelet layer 18. These buffy coat constituent layers 14, 16, and 18 will be differentially colored because of a flourencent stain which is added to the blood sample prior to centrifugation. Above the buffy coat constituents is the plasma layer 20, which is basically water. The correction band is denoted by the numeral 22, and is composed of a predetermined volume of plastic beads which have a mean specific gravity of about 1.035. The actual volume of the beads in the tube 2 is relatively unimportant, so long as enough beads are included to create a change in the length of the band 22 which is able to mirror significant variations in the thickness of the annulus between the tube 2 and float 8, which variations are caused by dimensional variations in the tube and float. When the tube and float are at their nominal target diameters, the length of the correction band will be assigned a value of 100 in the microprocessor software. Thus, if the annulus has a thickness that is less than the nominal target thickness, then the correction band will be longer than the assigned 100 value. If, for example, the measured band length is 110, then the microprocessor will know that the other true band lengths will be calculated by dividing their apparent lengths, as measured, by 1.10, the relative measured length of the correction band. The microprocessor will be preprogrammed to perform this correction calculation for all of the measured layers. It will be appreciated that this use of a correction band which reflects variations from the norm in the annulus will result in accurate and true constituent layer measurements.

An example of the operation of this invention is as follows. A blood sample when run in a tube and float combination which had been formed with the target dimensions to produce an annulus of normal thickness displayed a hematocrit of 470; a granulocyte count of 4.0; a lymphocyte/monocyte count of 2.0; a platelet count of 350; and a control band of 100. When the same sample is run in a tube which is 0.00016 inch oversized in its bore, and a float which has an OD which is 0.00011 undersized, the following apparent counts will be made. The hematocrit count will measure 46.9; the granulocyte count will measure 3.68; the lymphocyte/monocyte count will measure 1.84; the platelet count will measure 322; and a control band count of 92. In every reading the microprocessor will compare the measured control band count to 100. Thus, the comparision between 92 and 10 is made, and the microprocessor calculates the appropriate correction factor and applies it to the other band measurements to determine and display the true WBC constituent (and total WBC) counts as well as the platelet count. It will be noted that the hematocrit amount is not significantly altered by errant annulus dimensions because of the thickness of the RBC band, and because the float does not sink into the red blood cells to a significant extent.

It will be readily appreciated that the technique of this invention will result in a considerable relaxation of manufacturing tolerances as applied to the tube bore diameter and the float OD. The use of the self adjusting control band provides the user with confidence that the displayed cell counts are accurate and statistically sound. The correction band is formed from microspheres which have a specific gravity that will ensure that the band will coalesce in an area in the tube which is outside of the constituent bands which are being measured. In a blood sample, for example, the red blood cells will have a mean specific gravity of about 1.0793; the granulocytes will have a specific gravity of about 1.0747; the lymphocyte/monocyte layer will have a specific gravity of about 1.0632; the platelets will have a specific gravity of about 1.0490; the beads, or other material forming the control will have a specific gravity of about 1.0350; and the plasma has a specific gravity of about 1.0280.

Since many changes and variations of the disclosed embodiment of this invention may be used without departing from the inventive concept, it is not intended to limit the invention otherwise than as required by the appended claims.

What is claimed is:

1. A method for determining whether an annulus has a radial thickness which deviates from a predetermined target thickness, said method comprising the steps of:
    (a) providing a transparent tube;
    (b) providing an elongated float in said tube, said float and said tube combining to form said annulus in said tube with the radial thickness of said annulus being defined by the difference between the ID of said tube and the OD of said float;
    (c) positioning a known volume of a flowable material in said annulus and confining said flowable material to said annulus so that said flowable material forms a reference band in said annulus which reference band has a length as measured axially of said tube which equals a predetermined standard target length when the radial thickness of the annulus equals predetermined target thickness; and
    (d) measuring the actual length of said reference band to determine whether the actual measured length of the band deviates from the standard target length thereby providing an indication of the manner and extent of any deviations of the annulus radial thickness from the predetermined target thickness of said annulus.

* * * * *